United States Patent [19]

Hübner et al.

[11] Patent Number: 6,040,354
[45] Date of Patent: Mar. 21, 2000

[54] IMPRESSION COMPOUND WITH A SILICON BASE AND WAX ADMIXTURE

[75] Inventors: Heijo Hübner, Wörthsee; Dierk Lübbers; Wolfgang Mühlbauer, both of Hamburg, all of Germany

[73] Assignee: Ernst Mühlbauer KG, Germany

[21] Appl. No.: 08/894,573

[22] PCT Filed: Feb. 21, 1996

[86] PCT No.: PCT/EP96/00723

§ 371 Date: Aug. 21, 1997

§ 102(e) Date: Aug. 21, 1997

[87] PCT Pub. No.: WO96/26246

PCT Pub. Date: Aug. 29, 1996

[30] Foreign Application Priority Data

Feb. 21, 1995 [DE] Germany ............................ 195 05 896
May 16, 1995 [DE] Germany ............................ 195 17 962

[51] Int. Cl.[7] ...................................................... A61K 6/10
[52] U.S. Cl. ........................... 523/109; 524/487; 524/488; 524/489; 524/763; 524/277; 524/279; 524/862; 524/863; 524/906; 264/16
[58] Field of Search ............................ 523/109; 524/906, 524/487, 488, 489, 763, 277, 279, 862, 863; 264/16

[56] References Cited

U.S. PATENT DOCUMENTS

| | | | |
|---|---|---|---|
| 3,137,665 | 6/1964 | Retford | 524/866 |
| 3,620,778 | 11/1971 | Morrell | 523/109 |
| 3,715,334 | 2/1973 | Karstedt | 260/46.5 UA |
| 3,775,352 | 11/1973 | Leonard, Jr. | 260/2.5 B |
| 3,814,730 | 6/1974 | Karstedt | 260/46.5 UA |
| 4,568,707 | 2/1986 | Voigt et al. | 523/109 |
| 4,778,832 | 10/1988 | Futami et al. | 523/109 |
| 4,879,339 | 11/1989 | Yoshino et al. | 524/740 |
| 4,990,561 | 2/1991 | Yoshioka | 524/763 |
| 5,462,587 | 10/1995 | Greenleaf et al. | 106/2 |

FOREIGN PATENT DOCUMENTS

| | | |
|---|---|---|
| 154 922 D1 | 9/1985 | European Pat. Off. . |
| 0 162 211 | 11/1985 | European Pat. Off. . |
| 0 166 107 | 1/1986 | European Pat. Off. . |
| 0 206314 | 12/1986 | European Pat. Off. . |
| 0 212144 | 3/1987 | European Pat. Off. . |
| 0 480238 | 4/1992 | European Pat. Off. . |
| 27 36 421 | 8/1977 | Germany . |
| 40 31 759 | 4/1992 | Germany . |
| 44 39 769 | 5/1996 | Germany . |
| 02 064 159 | 3/1990 | Japan . |

*Primary Examiner*—Margaret G. Moore
*Attorney, Agent, or Firm*—Medlen & Carroll, LLP

[57] ABSTRACT

An impression composition which is based on an aziridine-free composition which can be vulcanized at room temperature, and which comprises wax is provided according to the invention. The wax increases the dimensional stability of the composition during mixing and curing. The invention furthermore provides a kit for the preparation of such compositions and a process for the preparation of the wax-containing components of these kits. The wax is dispersed throughout the composition and is prepared by shock-cooling. The wax forms a crystalline network.

44 Claims, 2 Drawing Sheets

A    B

A    B

IMPRESSION COMPOUND WITH A SILICON BASE AND WAX ADMIXTURE

FIELD OF THE INVENTION

The invention relates to a composition which can be vulcanized at room temperature and is based on polysiloxanes, polysulphides and/or aziridine-free polyethers, its use as an impression material and its manufacture.

BACKGROUND OF THE INVENTION

In dentistry, a dental prosthesis is produced with the aid of models. Such a working model must reproduce the teeth and jaw true to the original. A three-dimensional negative of the jaw situation is first produced with the aid of an impression material. For this, the impression material, in its plastic state, is introduced into the mouth of the patient with an impression tray, and solidifies there to form an elastic composition, which is the negative mould after removal. The working model is obtained by filling this impression with a modelling material. Impression materials which are used are, for example, compositions based on alginates, polysulphides, silicones and vulcanizable polyether materials.

These compositions have various properties and have advantages and disadvantages for each type of use on the basis of their processability, their physical properties, their quality of impression and taking reproduction and their cost.

Such impression materials which can be vulcanized at room temperature are prepared by mixing a composition comprising one or more components, usually and more favourably two, at least one base component and one hardener or initiator or catalyst component. The base component and hardener are basic components of the composition. The rubber-elastic solidification which occurs after mixing is called vulcanization, polymerization, setting or curing.

Impression materials of synthetic polymers based on polysiloxanes (silicones) are widespread. They are crosslinked to an elastomer by a chemical reaction. In the case of silicone materials, a distinction is made between condensation-crosslinking and addition-crosslinking silicone compositions. The condensation-crosslinking silicones as a rule crosslink by titanium- or tin-catalysed reaction of the polysiloxane having hydroxyl end groups with alkoxy-silicone compounds, an alcohol being split off. In the case of the addition-crosslinking silicones, crosslinking is effected as a rule by platinum-catalysed reaction of unsaturated hydrocarbon end groups of the polysiloxane with Si—H groups of a hydridopolysiloxane (hydrosilylation). Such silicone impression materials are known, for example, from EP-A-0 162 211, DE-A-40 31 759 and EP-A-0 166 107. The silicone compositions are as a rule supplied as a two-component system, and after the components have been mixed, the composition formed is introduced into the mouth of the patient and cures there within a period of usually 3–5 minutes.

One disadvantage of the known vulcanizable compositions is that they have a relatively low dimensional stability in the uncured state. Although this can be improved by compounding with suitable, chemically compatible fillers and additives (for example addition of pyrogenic silicic acids or a high degree of filling of the paste with coarse inorganic fillers), this is also usually associated with thixotropic properties or a loss of detail reproduction of the paste while taking the impression. This means that while applying pressure in taking the impression, either the materials tend to yield to the pressure and flow away or fine details cannot be reproduced. Because of this property, the penetration capacity of the silicone impression materials into gaps, which is important for the reproduction of the details in the mouth, is not particularly good.

SUMMARY OF THE INVENTION

The invention is based on the object of providing a vulcanizable composition of the above-mentioned type which has an improved dimensional stability and gap penetration capacity in the uncured state and therefore does not have the disadvantages mentioned or has them only to a small degree.

This means, during mixing (for example by means of a spatula on a mixing pad), the components of the impression composition should flow readily. After mixing, however, the composition should as far as possible acquire dimensional stability, and in particular the mixed composition should not flow from the mixing pad or the dental tray when this is turned upside-down for the purpose of taking an impression in the lower jaw, but at the same time should not yield to the pressure, but rather should press into the details of the situation in the mouth. With conventional impression compositions of the prior art, however, these properties do not exist to the desirable degree.

A composition based on polysulphides, silicones and/or vulcanizable aziridine-free polyether material is provided according to the invention, which is characterized by a content of at least one wax, with the exception of hydrogenated castor oil, paraffin waxes and microwaxes.

DEFINITIONS

The term wax in the context of the invention is intended to include all substances and substance mixtures which have the following properties:

kneadable, firm to brittle hard at 20° C., coarsely to finely crystalline, translucent to opaque, but not vitreous, melts above 40° C. without decomposition, relatively low viscosity just slightly above the melting point or softening point, highly temperature-dependent in consistency and solubility, polishable under gentle pressure.

This definition is taken from Ullmanns Encyklopädie der technischen Chemie [Ullmans Encyclopedia of Industrial Chemistry], 4th edition, Verlag Chemie, Weinheim, Volume 24, page 3 and is a recognized definition of waxes among experts. Paraffin waxes and microwaxes, that is to say waxes which are prepared petrochemically by fractionation of crude oil, are excluded from the subject matter of the claims relating to the substance and the kits described below in more detail for its preparation. Paraffin waxes and microwaxes are described in detail in the above-mentioned Ullmanns Encyklopädie [Ullmans Encyclopedia], Volume 24, pages 22–24. The following waxes, for example, can be used according to the invention:

plant waxes, such as: carnauba waxes, candelilla waxes, ouricori waxes, sugar cane waxes, retamo waxes;

animal waxes, such as beeswax, other insect waxes or wool wax;

montan waxes and polyolefin waxes.

A description of suitable waxes is given in the above Volume 24 of Ullmans Enzyklopädie [Ullmans Encyclopedia] on pages 2–20 and 36–47. By reference thereto, these literature references become the subject matter of the disclosure of this application.

Important constituents of the waxes are as a rule one or more of the following components:

hydrocarbons, chiefly saturated alkanes with a low degree of branching; alkyl esters; alkyl ethers; primary alcohols; acids; ketones; aldehydes; secondary alcohols; hydroxy acids; lactones; acetals; diols, chiefly α,ω-diols; dicarboxylic acids; diketones; polyesters.

Animal or plant fats, and optionally hydrogenated or chemically modified fats, which fall under the above-mentioned definition of waxes can also be used according to the invention. An overview of fats is to be found in Ullmanns Encyklopädie der technischen Chemie [Ullmans Encyclopedia of Industrial Chemistry], 4th edition, Volume 11, pages 457–524. By reference thereto, this literature reference also becomes the subject matter of the disclosure of this application. Optionally hydrogenated beef tallow has proved to be a wax which is particularly suitable for the purposes of the invention.

DETAILED DESCRIPTION OF THE INVENTION

The compositions according to the invention have good Theological properties. When used as an impression composition, they flow with a low viscosity under a slight pressure to the model to be reproduced. They thus stay unchanged and remain firm until they harden to their rubber-elastic state; Intermediate creep from the oral surface to be reproduced not take place or takes place only to a small degree.

The action of the waxes used according to the invention probably consists in the wax forming a crystalline network (microfine crystal or needle felt mesh) in the composition which can be vulcanized at room temperature, and this network reduces the tendency of the composition to flow away under pressure and thus increases the dimensional stability. It is indeed already known from EP-A-0 166 107 to mix paraffin waxes or microwaxes into silicone impression materials. Because of their poor tendency towards crystallization, these microwaxes cannot improve the dimensional stability of the composition by formation of a crystalline network, on the contrary, according to EP-A-0 166 107, they have such a low melting range that they melt or at least become soft due to the energy supplied during mixing and kneading of the composition, and in this way prevent tackiness of the composition. The object to be achieved and the technical action of the paraffin waxes or microwaves added according to EP-A-0 166 107 are accordingly different to those in the present invention.

An addition-crosslinking composition based on polysiloxanes which comprises hydrogenated castor oil as a structure-forming agent is known from EP-A-0 154 922. The doctrine of this specification is to incorporate hydrogenated castor oil (melting point 85° C.) into the composition, while heating to 95° C., and cooling the composition to 25° C., while stirring. Experiments carried out by the inventors of the present application have shown that exclusively hydrogenated castor oil, but not other waxes, is suitable as a structure-forming agent according to this technical doctrine. The present invention has recognized that any waxes are suitable for achieving the action desired according to the invention if the compositions are prepared by the process according to the invention described below. It is essential for the success of the invention that, after a solution or emulsion of wax and composition, which can be vulcanized at room temperature, has been prepared by dispersion, a relatively rapid cooling (shock cooling) of the emulsion or solution takes place, preferably by application onto a cold surface. This shock cooling surprisingly has the effect that compositions having the properties desired according to the invention can be prepared with addition of any wax.

The wax content of the composition is advantageously 1–40% by weight, preferably 2–15% by weight, more preferably 5–10% by weight. The waxes according to the invention are preferably used in polysiloxanes and can be employed for both addition-crosslinking and in the case of condensation-crosslinking polysiloxanes. The composition which can be vulcanized at room temperature is used as an impression, duplicating or modelling composition in particular, but not exclusively, in the dental field.

The melting point or softening range of the waxes used according to the invention is preferably between 40 and 250° C., and is preferably 40 to 200° C., more preferably 40 to 100° C., 40 to 80° C., and 40 to 70° C. is particularly preferred.

The molecular weight of the waxes used is preferably below 2000. It is furthermore preferable if the waxes used contain ester groups. Both the features mentioned help to improve the crystallization ability of the wax or waxes.

The term "composition based on polysiloxanes, polysulphides and/or aziridine-free polyethers" used in the claims is intended to include all compositions in which, after crosslinking, the polymeric network includes chiefly polysiloxanes, polysulphides and/or aziridine-free polyethers. The term therefore also includes, in particular, those compositions in which, for example, the weight content of fillers and auxiliaries added is greater than that of the polysiloxanes, polysulphides and/or aziridine-free polyethers.

Dental impression materials based on silicones are usually marketed as a kit, which as a rule has two or three components. After the components have been mixed in the envisaged ratio, crosslinking starts and the composition can be cured to an elastic mould within a few minutes (usually 3–5 minutes).

The invention also relates to kits for the preparation of a composition according to one of claims 2–6. For the purpose of preparation of an addition-crosslinking polysiloxane composition, according to the invention two components of the kit in each case have the following constituents:

Component 1
polysiloxanes having at least two unsaturated hydrocarbon groups, preferably vinyl groups, in the molecule,
hydridopolysiloxanes having at least two Si—H groups in the molecule,
waxes, with the exception of hydrogenated castor oil, paraffin waxes or microwaxes,
if appropriate, customary fillers and additives, auxiliaries and dyes, Component 2
if appropriate, polysiloxanes having at least two unsaturated hydrocarbon groups, preferably vinyl groups, in the molecule,
catalyst,
if appropriate, waxes, with the exception of hydrogenated castor oil, paraffin or microwaxes,
if appropriate, customary fillers and additives, auxiliaries and dyes.

Component 1 comprises the two polysiloxane components which can be crosslinked with one another, that is to say the polysiloxanes provided with reactive double bonds (as a rule vinyl end groups), preferably so-called polysiloxanes blocked by vinyl end groups, and the hydridopolysiloxanes provided with reactive Si—H groups. Component 1 furthermore comprises the added wax according to the invention and as a rule customary fillers, such as, for example, powdered quartz and β-cristobalite flours, calcium sulphate and carbonate, diatomaceous earth and pyrogenic silicic acid. The content of these fillers is usually between 5 and 60% by weight.

The additives and auxiliaries can be, for example, customary plasticizers, paraffin oils or the like, and they can furthermore also be polysiloxanes without reactive groups, which thus cannot participate in the crosslinking reaction. Polysiloxanes blocked by trimethylsilyl end groups, for example, can be used for this purpose.

Dyes are employed, in particular, to differentiate between the two components (base paste and catalyst paste) and to control mixing. Inorganic or organic coloured pigments are used as a rule.

The polysiloxanes contained, if appropriate, in component 2 and the waxes, fillers and other additives present, if appropriate, correspond to the constituents just described.

The catalyst is preferably a platinum complex, which can be prepared, for example, from hexachloroplatinic (IV) acid. However, any other platinum compound or another catalyst compound which accelerates the addition crosslinking reaction is also suitable. Platinum siloxane complexes, which are described, for example, in U.S. Pat. No. 3,715,334, U.S. Pat. No. 3,775,352 and U.S. Pat. No. 3,814,730, are particularly suitable.

The wax incorporated into component 2, if appropriate, should be chosen with respect to chemical compatibility with the catalyst used, especially if a relatively long storage stability of the components is desired, so that this catalyst does not become inactive prematurely. Customary catalyst inhibitors can also be added, if appropriate, as additives in order to increase the storage stability of the catalyst paste.

The wording used in the claims that the kit comprises two components does not mean the list of the components of a kit according to the invention is exhaustive. Additional components can be present, if appropriate.

The addition-crosslinking kit is advantageously designed such that the base paste and catalyst paste are mixed with one another in a ratio of 1:1. This represents a substantial facilitation during mixing of the composition, since it is then merely necessary to mix strands of the two pastes of the same length with one another. The wax content in each of the two components is then advantageously between 1 and 40% by weight, preferably between 2 and 15% by weight, more preferably between 5 and 10% by weight. The filler content in both components is then also advantageously between the values of 5 and 60% by weight already mentioned.

It should be noted that the ratio of the amounts of the two components may vary. Thus, for example, it is not absolutely essential for the catalyst paste also to comprise waxes. For example, if the pastes are formulated such that only small amounts of the catalyst paste must be mixed with the base paste, an addition of wax to the catalyst paste is not necessary. In this kit, it is decisive only that the two polysiloxane components which crosslink with one another and the catalyst must not be contained in one component from the beginning. In the context of the invention, component 2 can thus also comprise exclusively a catalyst.

In a kit according to the invention for the preparation of a condensation-crosslinking silicone composition, the two components in each case have the following constituents:

Component 1
polysiloxanes having at least two hydroxyl groups in the molecule,
waxes, with the exception of paraffin waxes or microwaxes,
if appropriate, customary fillers and additives, auxiliaries and dyes,
Component 2
polyalkoxysilicates having at least two alkoxy groups in the molecule,
catalyst,
if appropriate, waxes, with the exception of paraffin waxes or microwaxes,
if appropriate, customary fillers and additives, auxiliaries and dyes.

The waxes and, if appropriate, the fillers and additives added are the same as described above in connection with the addition-crosslinking silicones. The polyalkoxysilicates contained in component 2 are silicic acid esters (as a rule ethyl esters) which have a crosslinking action and can undergo condensation with the hydroxyl groups of the polysiloxane contained in component 1 under the action of the catalyst, alcohol being split off.

Organic tin or titanium compounds, such as tin octoate or dibutyltin dilaurate are used, for example, as a catalyst for the condensation reaction.

In the case of the condensation-crosslinking kits, as a rule the catalyst paste (component 2) is admixed to the base paste (component 1) in a significantly lower ratio than 1:1. For example, a mixing ratio of 1:10 is customary. It will therefore often not be necessary to add waxes and other fillers and additives to component 2. In the context of the invention, it is therefore also possible to employ a commercially available catalyst paste as component 2 in the condensation-crosslinking systems. It is furthermore possible in the context of the invention for the polysiloxanes having at least two hydroxyl groups in the molecule on the one hand and the polyalkoxysilicates on the other hand to be constituents of one component and for the catalyst to be the constituent of a second component.

The wax content of components 1 and/or 2 is advantageously such that after mixing of these in the envisaged ratio, a wax content of 1–40% by weight, preferably 2–15% by weight, more preferably 5–10% by weight, is established in the resulting composition.

In the kits described, storage stability is achieved, inter alia, by the base components and catalyst components which participate in the polymerization reaction or initiate this reaction are stored physically separated from one another. Alternatively, it is conceivable not to separate these components physically from one another, but to store them under conditions which exclude polymerization, such as, for example, exclusion of air, moisture and/or light. Storage stability furthermore means that the constituents of the components of the kit are stable towards separation and undergo no chemical reaction with one another under customary ambient conditions (atmospheric pressure and temperatures up to 30° C.) until they are provided for mixing as specified.

The invention furthermore relates to a process for the preparation of the wax-containing components of a kit for the preparation of an aziridine-free composition which can be vulcanized at room temperature. It comprises the following process steps:

heating of a mixture of polysiloxanes, polysulphides and/or aziridine-free polyether materials and of wax and, if appropriate, of fillers, additives, auxiliaries and dyes to a temperature above the melting point of the wax or waxes, preparation of an emulsion of wax and polysiloxanes, polysulphides and/or aziridine-free polyether materials by dispersion, shock cooling of the emulsion, if appropriate, mixing of further fillers, additives, auxiliaries and dyes into the cooled composition.

The envisaged heating of the mixture to a temperature above the melting point of the wax is initially decisive for the success of the process according to the invention. If the wax used does not have a sharp melting point but has a relatively broad melting range, this feature is to be interpreted such that the mixture is heated to a temperature above this melting range. The wax must be completely converted into the liquid phase. A crystalline network that may have been present beforehand in the solid phase of the wax must be at least largely destroyed.

Since the wax on the one hand and polysiloxanes, polysulphides and/or aziridine-free polyether materials on the other hand as a rule do not dissolve in one another, a two-phase mixture is now present, which must be converted into an emulsion by dispersion. If the constituents of the mixture dissolve in one another, the dispersing step can be dispensed with. If the mixture already comprises other fillers or additives, these are either dissolved in one of the two phases or dispersed in the mixture. However, as a rule it is advantageous to add inorganic fillers in particular only in the last above-mentioned process step. If appropriate, the formation and stabilization of the emulsion can be assisted by known and customary surface-active substances, such as emulsifiers, emulsion stabilizers or pyrogenic silicic acids.

In the next process step, the emulsion or solution prepared is shock-cooled. During the cooling, the temperature falls below the melting point or melting range of the wax. Cooling is carried out rapidly (shock cooling), for example by applying the emulsion to a cold surface, such as a cooling roll. During shock cooling, the wax contained in the mixture forms a crystalline network which penetrates the composition completely and thus leads to an improved dimensional stability of the composition according to the invention. It is particularly advantageous if a clear solution or solids-free emulsion is present before the shock cooling and the wax crystallizes out and forms the crystalline network during shock cooling only.

An advantageous continuous industrial process for shock cooling is application of the hot solution or emulsion onto a single to triple roller mill which can readily be cooled, if appropriate under an inert gas or with exclusion of air. The amount of solution or emulsion dispensed and the operating conditions of the roller mill are preferably chosen such that the shock-cooled preliminary mixture removed has a temperature which is not substantially above room temperature. The removal temperature can advantageously be adjusted by the thickness of the layer which is applied and is to be shock-cooled and the change in the peripheral speed of the cooling rolls.

If appropriate, further customary fillers, auxiliaries, additives and dyes can be introduced into the cooled composition with the aid of customary compounding methods. It is often advantageous to leave the preliminary mixture to rest and mature at a temperature of less than 20° C. for 24 hours, before incorporating the additives.

The compositions prepared by the process according to the invention show good rheological properties. The components of a kit can easily be mixed homogeneously during mixing, and the viscosity of the components of the kit is low. The homogenized and as yet uncured impression composition obtained after mixing of the components shows little or no cobwebbing, and has an adequate firmness, so that it does not flow from the dental tray. The composition that has not yet polymerized can be introduced by means of a fine-nozzle syringe into hollow cavities and undercut sections of the model of which an impression is to be taken.

The impressions produced with the impression materials according to the invention have a good detail reproduction. When used in the oral field, the impression compositions according to the invention are easily removable due to their relative hydrophobicity.

The wax-containing components for the preparation of the impression compositions according to the invention show a finely polycrystalline structure when observed as a thin layer under a transmitted light microscope under polarized light. This polycrystalline structure disappears on heating. If slow cooling then takes place, the material shows a very much coarser crystalline structure. The process is reversible, and during subsequent heating and shock cooling the original finely crystalline structure forms again. Observation by means of a transmitted light microscope is thus also suitable for quality control and monitoring of production.

BRIEF DESCRIPTION OF THE DRAWINGS

The invention is explained below with the aid of examples. The attached figures show.

EXAMPLE 1

Figure 1:
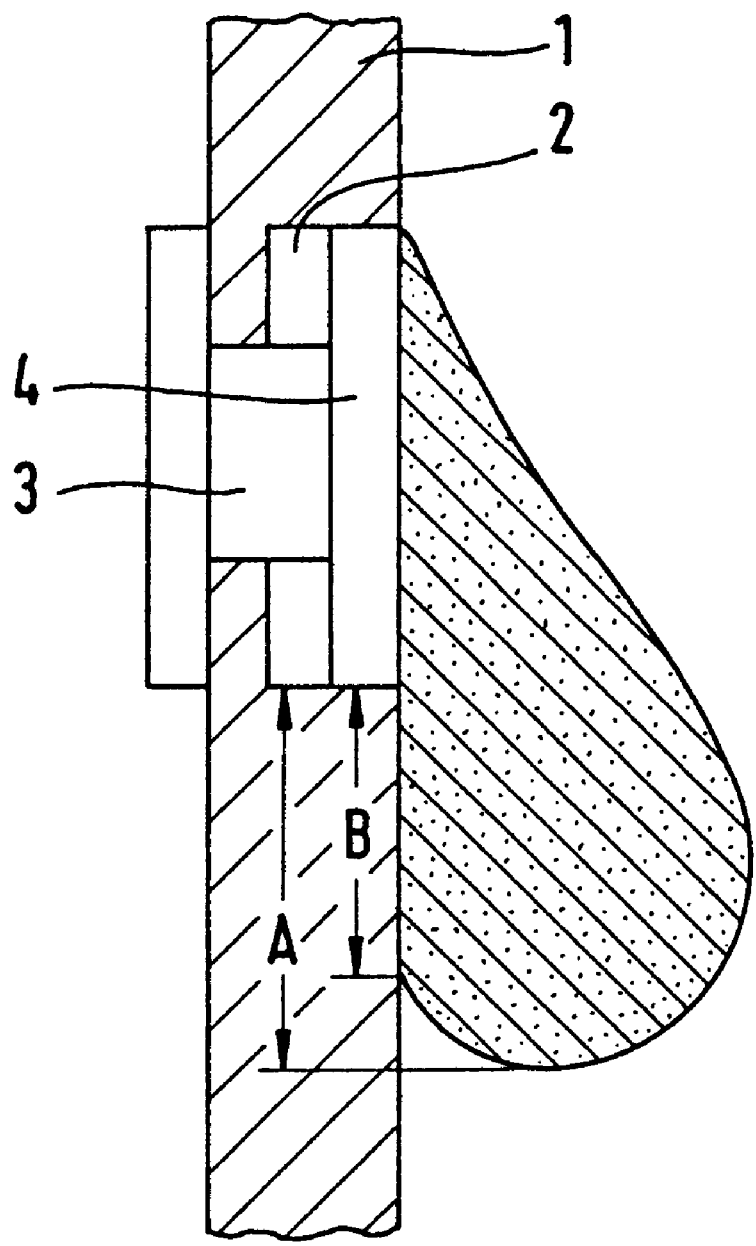
FIG. 1 a diagram of a device for testing the dimensional stability of a silicone composition.

The base paste and catalyst paste for an addition-crosslinking silicone composition according to the invention are prepared as follows:

Base Paste 113 g of polydimethylsiloxane blocked by vinyl end groups and having a viscosity of 1000 mPas, 57 g of polydimethylsiloxane blocked by vinyl end groups and having a viscosity of 65,000 mPas, 14 g of polydimethylsiloxane blocked by vinyl end groups and having a viscosity of 165,000 mPas (Silopren U1, U65 and U165, Bayer AG, Leverkusen), 19 g of paraffin (paraffin, per liquidum, Pioneer 2076, Hansen & Rosenthal, Hamburg), 5 g of ethoxylated fatty alcohol (Lutensol A3, BASF AG), 22 g of pyrogenic silicic acid HDKH 2000/4 (Wacker AG), 13 g of polyhydridosiloxane having a content of SiH groups of 4.3 mmol/g and 25 g of hydrogenated beef tallow Ewanol HY 2 (trade name of E. Wagner, Bremen) are weighed into a 500 ml glass beaker and heated at 150° C. for one hour in a heating cabinet.

The batch is then stirred in the hot state with a disperser for 2 minutes until homogeneous and heated again at 150° C. in the heating cabinet for 30 minutes. In the hot state, the resulting composition is passed over a triple roller mill (EXAKT 50, Exakt Apparatebau, Norderstedt, roller diameter 50 mm, roller length 15 cm). The rollers are operated at room temperature and a very low speed of rotation. The resulting resin mixture is then allowed to mature overnight at room temperature. On the following day, a filler mixture of 15 g of kieselguhr, 63 g of β-cristobalite Sikron SF 6000 (Quarzwerke Frechen) and 146 g of Sikron SF 8000 is incorporated into the resin mixture using a planetary kneader.

The paste shows a particular dimensional stability, which manifests itself, for example, by the fact that structures formed on the mixing block have not merged even after some days.

Catalyst Paste

Analogously to the procedure for the preparation of the base paste, 117, 96 and 11 g of polydimethylsiloxanes blocked by vinyl end groups and having a viscosity of 1000, 65,000 and 165,000 mPas, 20 g of paraffin (paraffin, per liquidum, Pionier 2076, Hansen & Rosenthal, Hamburg), 5 g of ethoxylated fatty alcohol (Lutensol A3, BASF AG) and 23 g of pyrogenic silicic acid HDKH 2000/4 with 25 g of Ewanol HY 2 (trade name of E. Wagner, Bremen) are melted, dispersed and passed over a triple roller mill. On the following day, 15 g of kieselguhr :PF5, Meyer-Breloh, Munster), 186 g of Sikron SF 6000, 20 g of Sikron SF 8000, 0.5 g of titanium dioxide (Kronos AV, Kronos, Leverkusen), 0.2 g of divinyltetramethyldisiloxane and 6.5 g of a complex of platinum and divinyltetramethyldisiloxane are incorporated into the resin mixture using a planetary kneader. The catalyst paste thus obtained has the same dimensional stability as the base paste in Example 1.

If this catalyst paste is mixed with the base paste in a weight ratio of 1:1, the mixture cures after a few minutes to give an elastic, tear-resistant mould with a Shore A hardness (after 24 hours) of about 50. The material has a linear shrinkage of less than 0.1% (determined in accordance with ISO 4823).

COMPARISON EXAMPLE 1

Not According to the Invention

Base Paste 113 g of polydimethylsiloxane blocked by vinyl end groups and having a viscosity of 1000 mPas, 57 g of polydimethylsiloxane blocked by vinyl end groups and having a viscosity of 65,000 mPas, 14 g of polydimethylsiloxane blocked by vinyl end groups and having a viscosity of 165,000 mPas, 19 g of paraffin, 5 g of ethoxylated fatty alcohol (Lutensol A3, BASF AG), 22 g of pyrogenic silicic acid HDKH 2000/4 and 13 g of polyhydridosiloxane having a content of SiH groups of 4.3 mmol/g are processed to a homogeneous paste with a filler mixture of 15 g of kieselguhr, 63 g of β-cristobalite Sikron SF 6000 (Quarzwerke Frechen) and 146 g of Sikron SF 8000 on a planetary kneader.

Catalyst Paste

Analogously to the procedure for the preparation of the base paste, 117, 96 and 11 g of polydimethylsiloxane blocked by vinyl end groups and having a viscosity of 1000, 65,000 and 165,000 mPas, 20 g of paraffin, 5 g of ethoxylated fatty alcohol (Lutensol A3, BASF AG) and 23 g of pyrogenic silicic acid HDKH 2000/4 are processed to a paste with 15 g of kieselguhr, 186 g of Sikron SF 6000, 20 g of Sikron SF 8000, 0.5 g of titanium dioxide, 0.2 g of divinyltetramethyldisiloxane and 6.5 g of a complex of platinum and divinyltetramethyldisiloxane using a planetary kneader.

If this catalyst paste is mixed with the base paste from Example 1 in a ratio of 1:1, the mixture cures after a few minutes to give an elastic, tear-resistant moulding having a Shore A hardness (after 24 hours) of about 50. The material has a linear shrinkage of less than 0.1% (determined in accordance with ISO 4823).

Figure 3:
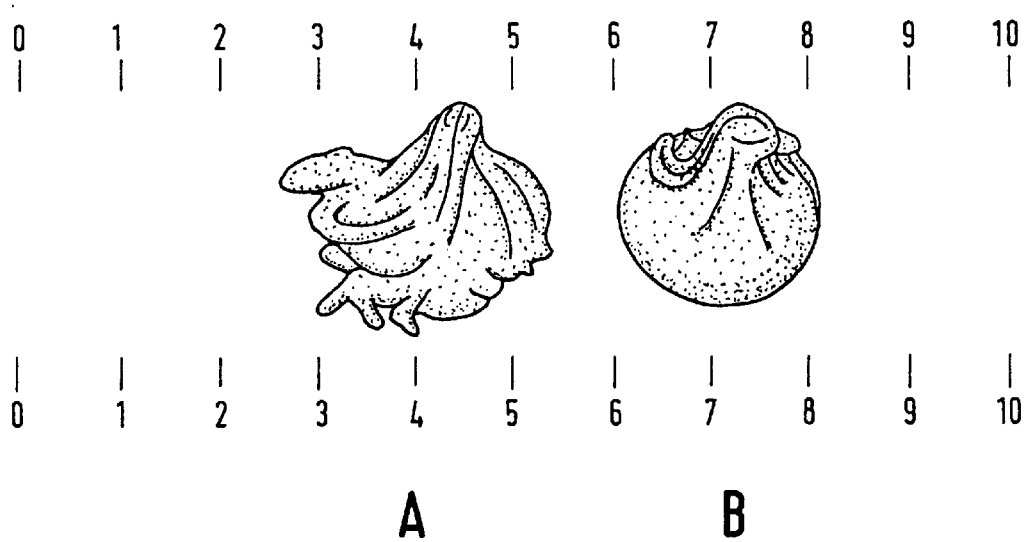
FIGS. 3, A and B, the result of testing the dimensional stability of the base paste of an addition-crosslinking silicone composition.

FIG. 3 shows the dimensional stability of the base paste prepared according to Example 1 (A) and the Comparison Example (B). It should be noted that comparable results are also obtained for the catalyst paste. Structures were formed in both base pastes on the mixing block with the aid of a spatula. FIG. 3 shows that these structures are still present in essentially unchanged form after one hour in the base paste according to the invention, whilst they have almost merged again in the base paste of the prior art.

EXAMPLE 2

This example shows a two-component system according to the invention for the preparation of a condensation-crosslinking silicone composition.

Base Paste 115 g of polydimethylsiloxane with hydroxyl end groups and having a viscosity of 2000 mPas, 119 g of polydimethylsiloxane with hydroxyl end groups and having a viscosity of 18,000 mPas (Silopren C2 and C18, Bayer AG, Leverkusen), 4 g of pyrogenic silicic acid HDKH 2000/4 (commercial product of Wacker) and 19 g of hydrogenated beef tallow Ewanol HY 2 (trade name of E. Wagner, Bremen) are weighed into a 500 ml glass beaker and heated at 140° C. in a heating cabinet for one hour. The batch is then stirred in the hot state for 2 minutes until homogenicity with a disperser and heated again at 140° C. in a heating cabinet for 30 minutes. In the hot state, the resulting composition is passed over a triple roller mill. The resulting resin mixture is then allowed to mature overnight at room temperature. On the following day, a filler mixture of 31 g of β-cristobalite Sikron SF 8000, 121 g of Silbond 8000 RST (Quarzwerke Frechen) and 3.6 g of coloured pigment is incorporated into the resin mixture using a planetary kneader. 1 g of distilled water, 5 g of glycerol and 2 g of silicone oil Silopren AC 3031 (commercial product from Bayer AG) are additionally stirred into the paste.

The paste shows about the same dimensional stability as the addition-crosslinking base paste according to the invention shown in FIG. 3 under A.

The commercially obtainable paste hardener "Silagum KV catalyst" (DMG, Hamburg) is used as the catalyst component and is mixed with the base paste in a weight ratio of 1:10. This catalyst is a mixture of alkoxylated polysilicates, tetraethyl orthosilicate, tin catalysts, vaseline, low viscosity paraffin and pyrogenic silicic acid. The mixture cures after a few minutes to yield an elastic, tear-resistant moulding having a Shore A hardness (after 24 hours) of about 40.

COMPARISON EXAMPLE 2

Not According to the Invention

Base Paste

The components from Example 2 were mixed to a paste in a planetary kneader, with the exception of the hydrogenated beef tallow Ewanol HY 2 and without the melting and cooling operation described. The resulting paste shows a significantly poorer dimensional stability than the paste from Example 2. Structures formed on the mixing block merge after a few hours.

The commercially obtainable paste hardener "Silagum KV catalyst" is used as the catalyst component and is mixed with the base paste in a weight ratio of 1:10. The mixture cures after a few minutes to yield an elastic, tear-resistant moulding having a Shore A hardness (after 24 hours) of about 40.

COMPARISON EXAMPLE 3

Not According to the Invention

Two organopolysiloxane mixtures, "mixture A" and "mixture B", are prepared according to DE-A 27 36 421 Example 1.

Mixture A (Catalyst Paste)

149 parts of an organopolysiloxane of 71.6 mol per cent of units of the formula $CH_3SiO_{3/2}$, 20.6 mol per cent of units of the formula $(CH_3)_2SiO$ and 7.8 mol per cent of units of the formula $CH_2=CH(CH_3)_2SiO_{1/2}$ having a viscosity of 97,000 cP at 25° C. are mixed with 2.62 parts of the mixture, comprising 1% by weight of platinum, of platinumdivinyltetramethyldisiloxane complex and dimethylpolysiloxane having a viscosity of 1400 cP at 25° C., the preparation of which has been described above, 1.64 parts of a 2% by weight solution of 1,3-divinyl-1,1,3,3-tetramethyldisiloxane in the above-mentioned organopolysiloxane with monomethylsiloxane units, 149 parts of quartz powder and 25 parts of a commercially available silicon dioxide produced pyrogenically in the gas phase and having a surface of 200 $m^2/g$, which is hydrophobized to the extent of 60% by treatment with dimethyldichlorosilane.

Mixture B (base paste)

121 parts of the organopolysiloxane with monomethylsiloxane units, which has been defined in more detail in connection with the description of the preparation of mixture A, are mixed with 50 parts of an organopolysiloxane, end-blocked by trimethylsiloxy groups, of 66.6 mol per cent of methylhydridosiloxane units and 33.4 mol per cent of dimethylsiloxane units having a viscosity of 80 cP at 25° C., 121 parts of quartz powder and 35 parts of the partly hydrophobized silicon dioxide defined in more detail in connection with the description of the preparation of mixture A.

Both mixture A and mixture B are spread individually onto a flat substrate or a mixing block. The two pastes are highly viscous and yield only reluctantly to the pressure of the mixing spatula. The pastes exhibit cobwebbing.

In a 1:1 mixture of A and B, the pastes can also be mixed only reluctantly with the spatula. The detail reproduction of oral surfaces, especially at transitions from teeth necks to the mucosa and so-called pockets, is low.

Both mixture A and mixture B can be extruded from an application syringe only with great effort. The same applies to the vulcanizing mixture immediately after mixing.

EXAMPLE 3

Preparation of the Crystal Line Network Pastes

As defined in more detail in the above-mentioned DE-A 27 36 421, Example 1, in each case an organopolysiloxane according to mixture A, without the platinum catalyst, and according to mixture B are mixed in equal parts and formulated to a viscosity of 25,000 mPa.s with polydimethylsiloxane blocked by trimethylsilyl end groups and having a viscosity of 50 cP (25° C.). 171 parts thereof, 5 parts of pyrogenic silicic acid and 17.1 parts of hydrogenated beef tallow having a softening point of 48–52° C. are then weighed into a container and heated at 60° C., with intensive stirring, until a homogeneous emulsion forms.

The emulsion thus obtained is then introduced in a thin jet onto a triple roller mill, which is not rotating too fast, the rollers of which are cooled internally. A colourless and opaque, stiff paste of 18 to 20° C. can then be removed at the third roller by a scraper.

The preliminary mixture thus obtained is left to rest in a cool place for one day.

Mixture According to the Invention 19 parts of quartz powder are then added to 188 parts of the preliminary mixture in a kneader with shearing forces which are not too high, and the resulting paste is then homogenized further and finally rendered bubble-free by vacuum kneading. The preparation is carried out under nitrogen as an inert gas.

The mixture thus obtained can be spread very easily onto a flat substrate or a mixing block. The paste can be moved easily and yields excellently to the pressure of the mixing spatula. On the other hand, it has an outstanding dimensional stability.

The paste tears off the spatula immediately when it is drawn out of the composition. It therefore exhibits no cobwebbing, and bubble-free mixing with the catalyst is ensured in an outstanding manner.

200 parts of the mixture can be mixed rapidly and easily with 2 parts of the platinum catalyst according to Example 1 from DE-A 27 36 421. The detail reproduction of oral surfaces, especially at transitions from teeth necks to the mucosa and so-called pockets, is outstanding.

The detail reproduction is particularly good if the mixed material is introduced into the niches and pockets of the model to be reproduced, using an application syringe and the model thus prepared is then put into the impression composition before the vulcanization.

The mixture can easily be applied from an application syringe. The same applies to the vulcanizing mixture immediately after mixing.

COMPARISON EXAMPLE AND EXAMPLE 4

A vulcanizable resin is prepared as defined in more detail in the so-called example according to the invention, Preparation of the resin, of DE-A 44 39 769.

COMPARISON EXAMPLE 4

770 parts of the resin described in DE-A 44 39 769 are kneaded to a paste, homogenized and rendered bubble-free with 210 parts of kieselguhr Celatom MW 25 and 20 parts of pyrogenic silicic acid Cabosil TS 610.

5.00 parts of the resulting paste are triturated homogeneously with 0.51 part of hardener paste on a mixing block in the customary manner, the pastes being difficult to mix using the spatula and tending to exhibit cobwebbing. The detail reproduction of oral surfaces, especially at transitions from teeth necks to the mucosa and so-called pockets, is poor.

The vulcanizing mixture immediately after mixing can be applied from an application syringe only with great effort.

EXAMPLE 4

800 parts of the resin described in DE-A 44 39 769 are homogenized intensively with 65 parts of a polytetrahydrofuran esterified with acetic acid at the end groups and having a molecular weight of 4500 and 5 parts of Cabosil TS 610 in a container at 80° C.

The hot preliminary mixture is then shock-cooled analogously to Example 1 according to the invention.

The preliminary mixture is then kneaded to a paste with 77 parts of kieselguhr Celatom, and then homogenized and rendered bubble-free.

5.00 parts of the resulting paste are triturated homogeneously with 0.51 part of hardener paste on a mixing block in the customary manner, the pastes being easy to mix with the spatula and not exhibiting cobwebbing. The detail reproduction of oral surfaces, especially at transitions from teeth necks to the mucosa and so-called pockets, is very good.

The vulcanizing mixture immediately after mixing can be applied very easily from an application syringe.

Determination of Dimensional Stability

To determine the dimensional stability of the mixed compositions with the same setting time, the testing device shown in the diagram in FIG. 1 was used. The testing device has a metal plate 1 having a cylindrical depression 2. A plunger 3 with a plate 4 can be moved backwards and forwards up to the front of the depression 2. In the extended position shown in FIG. 1, the plate 4 is flush with the surface of the metal plate 1 shown on the right in FIG. 1. By pushing the plunger 3 to the left in FIG. 1, a cylindrical depression is created in the metal plate 1.

To charge the testing device, it is positioned such that the depression 2 faces upwards and the plunger 3 is withdrawn into the depression. The part of the depression 2 exposed by the plate 4 is filled with a composition of the base paste and catalyst paste, mixed in the envisaged ratio, and the composition is spread smoothly. About 20–60 seconds after the start of mixing (in the present examples 60 seconds after the start of mixing), the testing device is brought into the vertical position shown in FIG. 1 and the plunger 3 is pushed to its forward position. The mixture is then left to cure.

The flow properties or the dimensional stability of the mixture is estimated from the zone A (the total flow zone of the mixture during the curing time) and B (flow zone during the curing time over which the silicone composition still remains in contact with the surface of the metal plate). The smaller the difference between A and B and the lower the absolute values of A and B, the greater the dimensional stability of the material.

Figure 2:
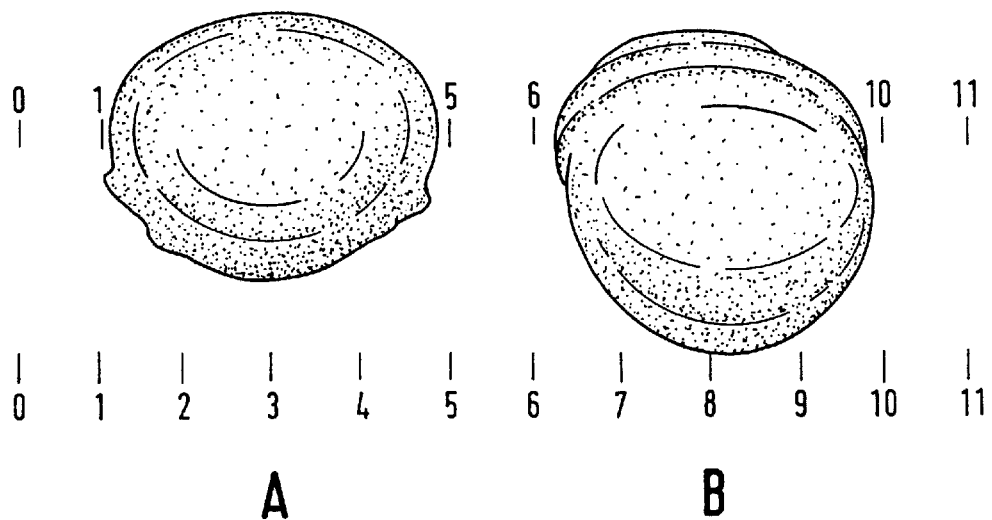
FIGS. 2, A and B, the result of testing the dimensional stability of a condensation-crosslinking silicone composition.

FIG. 2 shows the flow properties measured in this way of a condensation-crosslinking silicone composition prepared according to Example 2 and Comparison Example 2. The dimensional stability of composition (A) according to the invention is 1 mm (zone A=4mm, zone B=3 mm). In contrast, the dimensional stability of Comparison Example 2 by this method is 2 mm (zone A=14 mm, zone B=12 mm). Similar measurements also result the compositions according to Example 1 and Comparison Example 1 (not shown in the figures).

We claim:

1. A composition, comprising at least one wax and at least one compound selected from the group consisting of polysiloxanes, polysulphides and aziridine-free polyethers, wherein said at least one wax is not hydrogenated castor oil, paraffin wax or microwax, wherein said composition is made by heating a mixture of said at least one wax and said at least one compound to a temperature above the melting point of said at least one wax, dispersing said mixture to provide an emulsion, and shock cooling said emulsion.

2. The composition of claim 1, wherein said composition comprises between 1% to 40% by weight of said at least one wax.

3. The composition of claim 2, wherein said composition comprises between 2% to 15% by weight of said at least one wax.

4. The composition of claim 3, wherein said composition comprises between 5% to 10% by weight of said at least one wax.

5. The composition of claim 1, wherein said molecular weight of said at least one wax is less than 2000.

6. The composition of claim 1, wherein said at least one wax comprises ester groups.

7. The composition of claim 1, wherein said polysiloxanes are addition-crosslinking polysiloxanes.

8. The composition of claim 1, wherein said polysiloxanes are condensation-crosslinking polysiloxanes.

9. A method for making an impression comprising the steps:
    a) providing said composition of claim 1; and
    b) making an impression with said composition.

10. A method for making a duplicate comprising the steps:
    a) providing said composition of claim 1; and
    b) making a duplicate with said composition.

11. A method for making a model comprising the steps:
    a) providing said composition of claim 1; and
    b) making a model with said composition.

12. A composition, comprising at least one wax and at least one compound selected from the group consisting of polysiloxanes, polysulphides and aziridine-free polyether materials, wherein said at least one wax is not hydrogenated castor oil, paraffin wax or microwax, wherein said at least one wax forms a crystalline network in said composition, and said composition can be vulcanized at room temperature.

13. The composition of claim 12, wherein said composition comprises between 1% to 40% by weight of said at least one wax.

14. The composition of claim 12, wherein said molecular weight of said at least one wax is less than 2000.

15. A method for making an impression comprising the steps:
    a) providing said composition of claim 12; and
    b) making an impression with said composition.

16. A method for making a duplicate comprising the steps:
    a) providing said composition of claim 12; and
    b) making a duplicate with said composition.

17. A method for making a model comprising the steps:
    a) providing said composition of claim 12; and
    b) making a model with said composition.

18. A kit, comprising:
    i) a first component comprising at least one polysiloxane having at least two unsaturated hydrocarbon groups, at least one hydridopolysiloxane having at least two Si—H groups, and at least one wax, wherein said at least one wax is not hydrogenated castor oil, paraffin wax or microwax, and wherein said at least one wax forms a crystalline network in said first component; and
    ii) a second component comprising a catalyst.

19. The kit of claim 18, wherein said first component further comprises at least one compound selected from the group consisting of fillers, additives, auxiliaries, and dyes.

20. The kit of claim 18, wherein said second component further comprises at least one polysiloxane having at least two unsaturated hydrocarbon groups.

21. The kit of claim 19, wherein said second component further comprises at least one wax, wherein said at least one wax is not hydrogenated castor oil, paraffin wax or microwax.

22. The kit of claim 20, wherein said second component further comprises at least one compound selected from the group consisting of fillers, additives, auxiliaries, and dyes.

23. The kit of claim 21, wherein said first component comprises at least one polysiloxane having vinyl groups.

24. The kit of claim 22, wherein said second component further comprises at least one polysiloxane having vinyl groups.

25. The kit of claim 23, wherein said first component and said second component each comprise 1% to 40% by weight of said at least one wax.

26. The kit of claim 24, wherein said first component comprises 2% to 15% by weight of said at least one wax.

27. The kit of claim 25, wherein said first component comprises 5% to 10% by weight of said at least one wax.

28. The kit of claim 24, wherein said second component comprises 2% to 15% by weight of said at least one wax.

29. The kit of claim 28, wherein, said second component comprises 5% to 10% by weight of said at least one wax.

30. A kit, comprising:
    i) a first component comprising at least one polysiloxane having at least two hydroxyl groups, and at least one wax, wherein said at least one wax is not hydrogenated castor oil, paraffin wax or microwax and wherein said at least one wax forms a crystalline network in said first component; and ii) a second component comprising at least one polyalkoxysilicate having at least two alkoxy groups, and a catalyst.

31. The kit of claim 30, wherein said first component further comprises fillers, additives, auxiliaries, and dyes.

32. The kit of claim 30, wherein said second component further comprises at least one wax, wherein said at least one wax is not paraffin wax or microwax.

33. The kit of claim 30, wherein said second component further comprises fillers, additives, auxiliaries and dyes.

34. The kit of claim 30, wherein said first component an said component each comprise 1% to 40% by weight of said at least one wax.

35. The kit of claim 34, wherein said first component comprises 2% to 15% by weight of said at least one wax.

36. The kit of claim 35, wherein said first component comprises 5% to 10% by weight of said at least one wax.

37. The kit of claim 34, wherein said second component comprises 2% to 15% by weight of said at least one wax.

38. The kit of claim 37, wherein said second component comprises 5% to 10% by weight of said at least one wax.

39. The kit of claim 30, wherein said polysiloxane is polydimethylsiloxane.

40. A process of making an impression compound, comprising the steps of:

a) providing:

i) at least one wax, wherein said at least one wax is not hydrogenated castor oil, paraffin wax, or microwax, and i) at least one compound selected from the group consisting of polysiloxanes, polysulphides and aziridine-free polyether materials;

b) heating said at least one wax and said at least one compound to a temperature above the melting point of said at least one wax to provide a mixture;

c) dispersing said mixture to provide an emulsion; and d) shock cooling said emulsion to provide a cooled dispersion.

41. The process of claim 40, further comprising the step of:

e) mixing fillers, additives, auxiliaries and dyes into said cooled dispersion.

42. The process of claim 40, wherein said step a) further comprises fillers, additives, auxiliaries and dyes, and wherein said heating of step b) further comprises heating said at least one wax, said at least one compound, said fillers, said additives, said auxiliaries and said dyes, to a temperature above the melting point of said at least one wax.

43. The process of claim 40, wherein said shock cooling step comprises application of said emulsion to a cold surface.

44. The process of claim 43, wherein said shock cooling step comprises application of said emulsion to a cooling roller.

* * * * *

UNITED STATES PATENT AND TRADEMARK OFFICE
CERTIFICATE OF CORRECTION

PATENT NO. : 6,040,354
DATED : 03/21/00
INVENTOR(S) : Heijo Hübner et al.

It is certified that error appears in the above-identified patent and that said Letters Patent is hereby corrected as shown below:

In column 3, line 23, please delete "Theological" and insert --rheological--.
In column 5, line 67, between "case" and "have" please insert --can--.
In column 6, line 48, please delete "not:" and insert --not--.
In column 9, line 14, please delete ":PF5" and insert --(PF5 --.
In column 13, line 29, between "result" and "the" please insert --for--.

IN THE CLAIMS:
In Claim 26, please delete "24" and insert --25--.
In Claim 27, please delete "25" and insert --26--.
In Claim 28, please delete "24" and insert --25--.
In Claim 34, please delete "an said" and insert --and said second--.

Signed and Sealed this

Twentieth Day of February, 2001

Attest:

NICHOLAS P. GODICI

Attesting Officer

Acting Director of the United States Patent and Trademark Office